United States Patent
Cao et al.

(10) Patent No.: US 11,382,683 B2
(45) Date of Patent: Jul. 12, 2022

(54) WIDE BAND MICROWAVE TISSUE ABLATION PROBE WITH VARIABLE LENGTH ANTENNA PARAMETERS

(71) Applicant: Boston Scientific Scimed, Inc., Maple Grove, MN (US)

(72) Inventors: Hong Cao, Maple Grove, MN (US); Timothy A. Ostroot, Cokato, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 218 days.

(21) Appl. No.: 16/738,532

(22) Filed: Jan. 9, 2020

(65) Prior Publication Data

US 2020/0222105 A1 Jul. 16, 2020

Related U.S. Application Data

(60) Provisional application No. 62/791,276, filed on Jan. 11, 2019.

(51) Int. Cl.
*A61B 18/14* (2006.01)
*A61B 18/18* (2006.01)
*A61B 18/00* (2006.01)

(52) U.S. Cl.
CPC .......... *A61B 18/14* (2013.01); *A61B 18/1815* (2013.01); *A61B 2018/00077* (2013.01);
(Continued)

(58) Field of Classification Search
CPC ................ A61B 18/14; A61B 18/1815; A61B 2018/00732; A61B 2018/183;
(Continued)

(56) References Cited

U.S. PATENT DOCUMENTS

| 6,051,018 A | 4/2000 | Larsen |
| 2016/0058508 A1 | 3/2016 | Brannan et al. |

(Continued)

FOREIGN PATENT DOCUMENTS

| CN | 113271882 | 8/2021 |
| WO | 2006084676 | 8/2006 |

(Continued)

OTHER PUBLICATIONS

Brace, Christopher "Microwave Tissue Ablation: Biophysics, Technoogy, and Applications," Critical Reviews in Biomedical Engineering, 38(1): 65-78 (2010) (14 pages).

(Continued)

*Primary Examiner* — Joseph A Stoklosa
*Assistant Examiner* — Adam J Avigan
(74) *Attorney, Agent, or Firm* — Pauly, DeVries Smith & Deffner LLC

(57) ABSTRACT

A variable-length microwave ablation probe is provided. The probe is configured to have a range of resonant frequencies. The probe includes a microwave antenna, an outer conductor, and a cap. The probe further includes a radiation window that is at least partially transparent to microwave energy. The distal boundary of the outer conductor or the proximal boundary of the cap varies in distance from the probe distal end. The probe can have a choke length, an arm length, a radiating portion length, and a cap length. The lengths can each affect the resonant frequency of the antenna. Some examples provide a variable choke length, a variable arm length, a variable radiating portion length, and/or a variable cap length.

20 Claims, 12 Drawing Sheets

(52) U.S. Cl.
CPC ........... *A61B 2018/00577* (2013.01); *A61B 2018/00732* (2013.01); *A61B 2018/183* (2013.01); *A61B 2018/1838* (2013.01); *A61B 2018/1853* (2013.01); *A61B 2018/1869* (2013.01); *A61B 2018/1876* (2013.01); *A61B 2018/1892* (2013.01)

(58) Field of Classification Search
CPC .......... A61B 2018/00077; A61B 2018/00577; A61B 2018/00023; A61B 2018/1876; A61B 2018/1838; A61B 2018/1853; A61B 2018/1869; A61B 2018/00529; A61B 2018/00511; A61B 2018/00541; A61B 2018/1892; A61N 5/02; A61N 5/025; A61N 5/045
USPC .......................................... 607/101
See application file for complete search history.

(56) References Cited

U.S. PATENT DOCUMENTS

| | | | |
|---|---|---|---|
| 2016/0151113 A1* | 6/2016 | Kim | A61B 18/18 606/33 |
| 2018/0261922 A1 | 9/2018 | Behdad et al. | |

FOREIGN PATENT DOCUMENTS

| | | | | |
|---|---|---|---|---|
| WO | WO-2006084676 A1 | * | 8/2006 | ......... A61B 18/1815 |
| WO | 2017103209 | | 6/2017 | |
| WO | 2020146699 | | 7/2020 | |

OTHER PUBLICATIONS

Cavagnaro, M. et al., "Design and Realization of a New Type of Interstitial Antenna for Ablation Therapies," 2009 European Microwave Conference (EuMC), Rome, 2009, pp. 878-881 (4 pages).

Cavagnaro, Marta et al., "A Minimally Invasive Antenna for Microwave Ablation Therapies: Design, Performances, and Experimental Assessment," IEEE Transactions on Biomedical Engineering, vol. 58, No. 4, Apr. 2011 (11 pages).

Coleback, Erin et al., "Ultra-Wideband Microwave Ablation Therapy (UMAT)," IEEE MT-S International Microwave Symposium Digest (2013) (3 pages).

"International Search Report and Written Opinion," for PCT Application No. PCT/US2020/013023 dated Apr. 30, 2020 (16 pages).

"International Preliminary Reporton Patentability," for PCT Application No. PCT/US2020/013023 dated Jul. 22, 2021 (10 pages).

"Response to Communication Pursuant to Rules 161(1) and 162 EPC," for European Patent Application No. 20704661.6 filed Aug. 10, 2021 (16 pages).

* cited by examiner

WIDE BAND MICROWAVE TISSUE ABLATION PROBE WITH VARIABLE LENGTH ANTENNA PARAMETERS

This application claims the benefit of U.S. Provisional Application No. 62/791,276 filed Jan. 11, 2019, the content of which is herein incorporated by reference in its entirety.

BACKGROUND

Microwave ablation (MWA) is a minimally invasive energy modality for body treatments in many locations, including soft tissue lesions in the liver, kidney and lung. Microwave ablation probes use an antenna, such as a monopole or dipole antenna, to radiate microwave energy into tissue for heating. Unlike radiofrequency ablation, which depends on ion movement and friction for heating, microwave ablation energy causes water molecules to rotate due to the polarity of the molecules and generates heat due to hysteresis. It typically operates at industrial, scientific and medical (ISM) radio bands such as 500 MHz to 10 GHz, and more specifically can operate at 945 MHz or 2.45 GHz. Microwave ablation has advantages such as fast heating, allowing the probe to operate at high temperature to create larger lesions, and has been gaining market share over the past decade over radiofrequency ablation (RFA) for tissue ablation.

SUMMARY

One general aspect includes a microwave ablation probe including a probe body, a coaxial cable within the probe body, and a cap. The probe body includes a shielded portion and a radiation window that is at least partially transparent to microwave energy. The coaxial cable includes a center conductor, a dielectric material surrounding the center conductor of the cable, and an outer conductor having an outer conductor distal boundary. The center conductor includes a radiating portion that extends beyond a distal boundary of the outer conductor, where the radiating portion is configured for emission of microwave energy, where the radiating portion is aligned with the radiation window. The cap is located at a probe distal end and includes a cap proximal boundary, where the outer conductor distal boundary or the cap proximal boundary varies in its distance from the probe distal end.

Implementations may include one or more of the following features. The probe where the outer conductor distal boundary varies in distance from the probe distal end. The probe where the cap includes a metallic material and the cap proximal boundary varies in distance from the probe distal end. The probe where the outer conductor distal boundary and the cap proximal boundary varies in distance from the probe distal end. The probe where the outer conductor distal boundary or the cap proximal boundary includes a plurality of discrete sections, where adjacent discrete sections are at different distances from the probe distal end. The probe where the outer conductor distal boundary or the cap proximal boundary includes a wave shape. The probe where the outer conductor distal boundary or the cap proximal boundary includes a saw tooth shape. The probe where the outer conductor distal boundary is a uniform distance from the probe distal end. The probe where the cap proximal boundary is uniform in distance from the distal end of the probe. The probe further including a choke. The probe where the shielded portion of the probe body includes a metal cannula. The probe further including a dielectric layer in between the metal cannula and the outer conductor. The probe further including a choke including: a choke contact between the metal cannula and the outer conductor, and a choke length extending between the choke contact and a distal end of the metal cannula. The probe where the choke contact or the distal end of the cannula varies in its distance from the probe distal end. The probe where the radiation window includes a portion of the dielectric material of the cable surrounding the radiating portion of the center conductor. The probe where the cap further includes a cap tip configured to pierce tissue at a cap distal end. Implementations of the described techniques may include hardware, a method or process, or computer software on a computer-accessible medium.

One general aspect includes a microwave ablation system including a microwave energy source and a microwave ablation probe. The probe includes a probe body, a coaxial cable within the probe body, a cap located at a probe distal end, and a choke. The probe body includes a shielded portion and a radiation window that is at least partially transparent to microwave energy. The probe body further includes a metal cannula. The coaxial cable within the probe body is connected to the microwave energy source. The cable includes a center conductor, a dielectric material surrounding the center conductor of the cable, and an outer conductor having an outer conductor distal boundary. The center conductor includes a radiating portion that extends beyond a distal boundary of the outer conductor, where the radiating portion is configured for emission of microwave energy, where the radiating portion is aligned with the radiation window. The cap includes a cap tip configured to pierce tissue at a cap distal end, and a cap proximal boundary. The choke includes a choke contact between the metal cannula and the outer conductor, and a choke length extending between the choke contact and a distal end of the metal cannula. The outer conductor distal boundary or the cap proximal boundary varies in its distance from the probe distal end. The outer conductor distal boundary may vary in distance from the probe distal end Implementations of the described techniques may include hardware, a method or process, or computer software on a computer-accessible medium.

One general aspect includes a method of microwave ablation including providing a microwave ablation probe and delivering microwave energy to a radiating portion of the probe. The probe includes a probe body including a shielded portion and a radiation window that is at least partially transparent to microwave energy. The probe also includes a coaxial cable within the probe body including a center conductor, a dielectric material surrounding the center conductor of the cable, and an outer conductor having an outer conductor distal boundary. The center conductor includes a radiating portion that extends beyond a distal boundary of the outer conductor, where the radiating portion is configured for emission of microwave energy, where the radiating portion is aligned with the radiation window. The probe includes a cap located at a probe distal end, the cap including a cap tip configured to pierce tissue at a cap distal end and a cap proximal boundary. The outer conductor distal boundary or the cap proximal boundary varies in its distance from the probe distal end. The probe may produce microwave energy at two or more resonant frequencies Implementations of the described techniques may include hardware, a method or process, or computer software on a computer-accessible medium.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope herein is defined by the appended claims and their legal equivalents.

Some of the figures are schematic in nature and are not drawn to scale. Certain features are shown larger than their scale and certain features are omitted from some views for ease of illustration. While embodiments are susceptible to various modifications and alternative forms, specifics thereof have been shown by way of example and drawings, and will be described in detail. It should be understood, however, that the scope herein is not limited to the particular aspects described. On the contrary, the intention is to cover modifications, equivalents, and alternatives falling within the spirit and scope herein.

DETAILED DESCRIPTION

The present disclosure provides a wide band microwave tissue ablation probe with variable length antenna parameters. By use of the term "variable" herein, it is meant that different portions of the antenna structure have different dimensions compared to neighboring portions.

Microwave antennas have a resonant frequency. The resonant frequency of the antenna affects the efficiency of the system, because when the resonant frequency is correctly tuned to the surrounding tissue, a high ratio of energy is transmitted into the tissue versus the amount of energy that is reflected. When the resonant frequency is not tuned, more energy is reflected, leading to less of the energy being transmitted into patient tissue.

Different portions of the antenna with different dimensions allow the antenna to be capable of more than one resonant frequency, such as two, three, four or more resonant frequencies. The antenna has multiple portions, each having a different resonant frequency. The single antenna acts as though it were multiple antennas in parallel.

Due to the limitations of microwave antennas within a microwave ablation probe, some of the microwave energy that is transmitted from the microwave energy source through the probe to the distal portion of the probe is reflected back from the distal portion of the probe toward the proximal portion of the probe. This decreases the efficiency of the probe, and can cause self-heating within the antenna. Reducing the amount of reflected energy can help reduce this self-heating.

Figure 1:
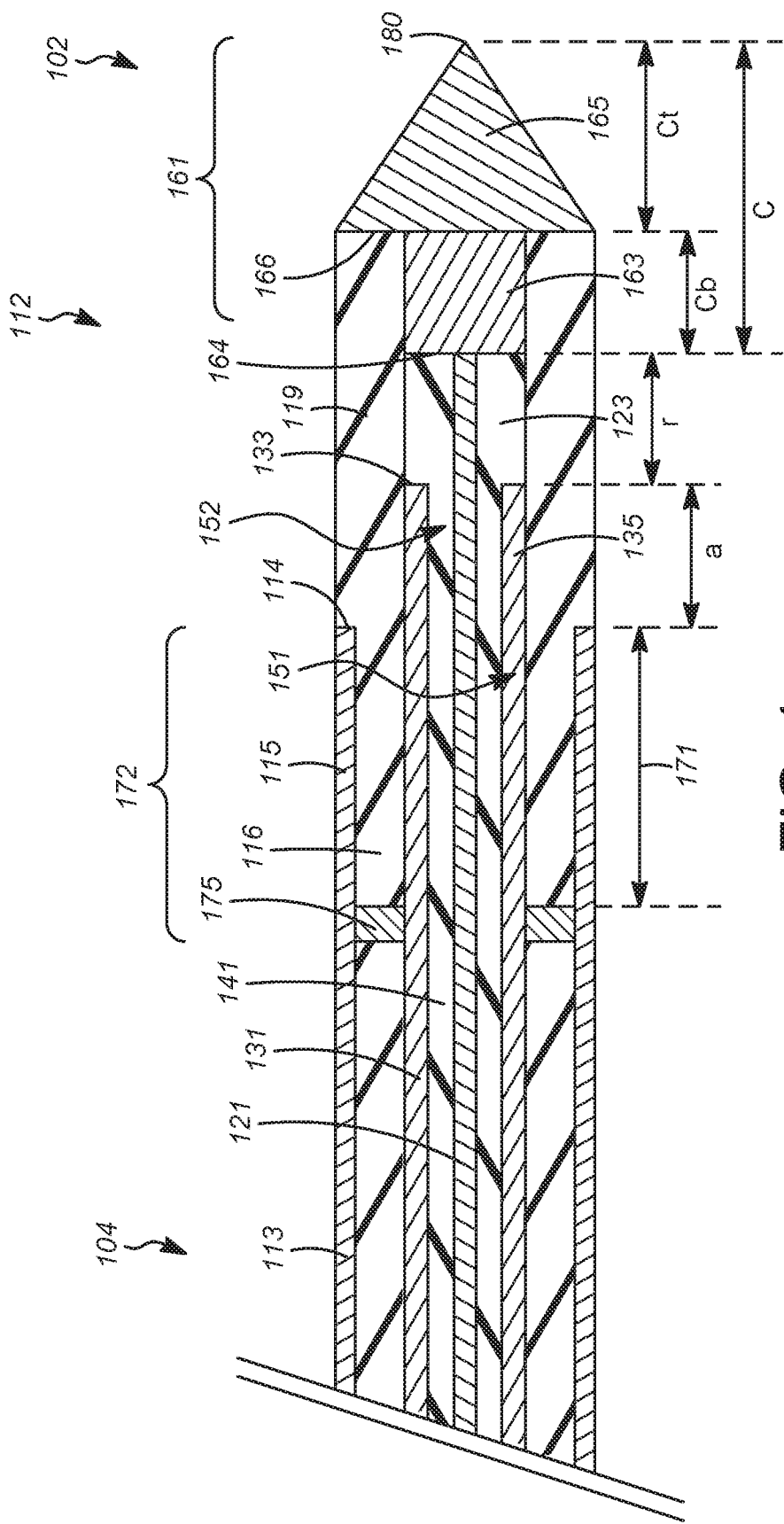
FIG. 1 is a cross-sectional view of a microwave ablation probe according to some examples.

A number of factors affect the resonant frequency of the probe. One factor is the length of the various portions of the antenna. Changes in these lengths can significantly affect the resonant frequency. The choke length, the arm length, the radiating portion length, the cap base length, and the cap tip length can each affect the resonant frequency. Each of these lengths are described in more detail below. FIG. 1 is a cross-sectional view of a microwave ablation probe demonstrating the parameters that can be changed to affect the resonant frequency of the probe.

Turning to FIG. 1, the probe 112 has a distal portion 102 and a proximal portion 104. As used herein, the words proximal and distal express a relationship between two different elements. An element that is designated as being proximal is positioned closer to the external portion of the system, i.e., a portion that does not enter a patient's body. An element that is designated as being distal is positioned closer to the insertion end of the system. In some examples, the probe 112 includes a cannula 113 having a cannula distal boundary 114 adjacent to a radiation window 119. The cannula 113 makes up part of a shielded portion 115 of the probe 112. At the distal portion 102 of the probe 112 is a cap tip 165. The radiation window 119 extends between the distal boundary 114 of the shielded portion 115 and the proximal boundary 166 of the cap tip 165.

The microwave antenna 152 includes a coaxial cable 151 with a center conductor 121, an outer conductor 131 coaxially surrounding the center conductor 121, and a dielectric 141 surrounding the center conductor 121 and separating the center conductor 121 from the outer conductor 131. Some examples of the technology also include a cap 161 at the distal portion 102 of the antenna 152. In some examples, the cap 161 includes a cap base 163 and a cap tip 165 adjoining the cap base 163 and distal to the cap base 163. In some examples, the cap tip 165 is a tissue-piercing trocar tip. The outer conductor 131 has a distal boundary 133 that abuts the radiating portion 123 of the antenna 152. The cap 161 has a proximal boundary 164 of the cap base 163 that abuts the radiating portion 123 opposite the distal boundary 133 of the outer conductor 131. The radiating portion 123 of the antenna 152 comprises an exposed portion of the dielectric 141 between the distal boundary 133 of the outer conductor 131 and the proximal boundary 164 of the cap base 163. In some examples, the probe 112 includes a choke 172 that includes a length 171 of the cannula 113 defined between a choke contact 175 and the distal boundary 114 of the cannula 113. The choke contact 175 electrically connects the cannula 113 to the outer conductor 131. The choke contact 175 can be a soldered connection, for example. The choke 172 further includes a dielectric 116 between the cannula 113 and the outer conductor 131. The dielectric 116 can be a polymer, or in alternative examples, the dielectric can be an air gap. The choke 172 is designed as a quarter wave reflector and acts as a barrier, preventing microwave energy from travelling back along the coaxial cable 151.

The ablation probe 112 comprises the shielded portion 115 surrounding and coaxial with the antenna 152. The radiation window 119 is aligned with the radiating portion 123 of the antenna 152. During an ablation procedure, microwave energy propagates in the dielectric 141, with the center conductor 121 and the outer conductor 131 as boundary constraints. At the distal end of the coaxial cable, the outer conductor 131 is removed so that the microwave energy can radiate into patient tissue to cause heating.

Antenna Parameters

The arm length, the radiating portion length, and the cap length can each affect the resonant frequency of the antenna. As used herein, the word length refers to a distance measured along or parallel to a longitudinal axis of the ablation probe. Still referring to FIG. 1, the arm 135 is a portion of the probe 112 in which the center conductor 121 is surrounded by the dielectric 141, which is surrounded by the outer conductor 131, and where the outer conductor 131 is surrounded by the radiation window 119. The arm 135 has an arm length a defined between the distal boundary 114 of the cannula 113 and the distal boundary 133 of the outer conductor 131. The choke 172 has a choke length 171 defined between the choke contact 175 and the distal boundary 114 of the cannula 113. The radiating portion 123 has a radiating portion r length defined between the distal boundary 133 of the outer conductor 131 and the proximal boundary 164 of the cap 161. The cap 161 has a cap length C defined between the proximal boundary 164 of the cap 161 and the probe distal end 180. The proximal boundary 164 of the cap 161 is also the proximal boundary of the cap base 163. The cap base 163 has a length Cb extending from its proximal boundary 164 to a proximal boundary of the cap tip 165. The cap tip 165 has a length Ct extending from a distal end of the cap base 163 to the probe distal end 180. The sum of Cb and Ct is the cap length C. The arm length and the cap length overlap with the inner conductor are parameters that can be varied to change the length of the radiating portion, and thereby change the resonant frequency of the antenna 152.

Figure 2:
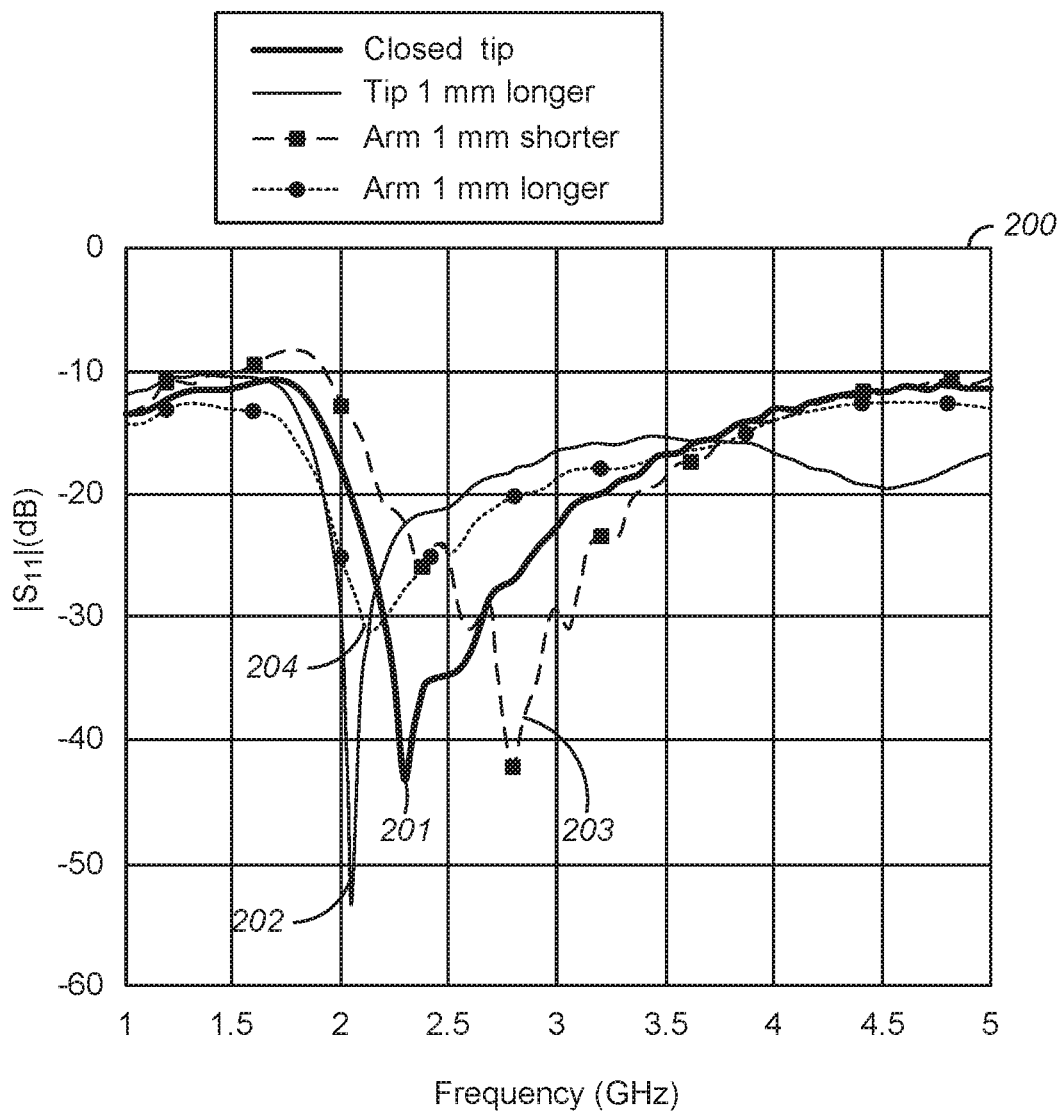
FIG. 2 is a graph showing the resonant frequency of microwave ablation probes having different antenna parameters.

Turning to FIG. 2, a graph 200 shows how the resonant frequency of the antenna can change when the dimensions of particular structures of the antenna are changed. The graph 200 shows the antenna reflection coefficient, $|S_{11}|$ in decibels plotted against frequency in Gigahertz. A decrease in the reflection coefficient indicates that more energy at that particular frequency is transmitted into tissue. The graph 200 is FIG. 5(a) from the article, Marta Cavagnaro et al., *A Minimally Invasive Antenna for Microwave Ablation Therapies: Design, Performances, and Experimental Assessment*, IEEE Transactions on Biomedical Engineering, Vol. 58, No. 4, April 2011 at 949, 954, which is incorporated by reference herein in its entirety. The antenna reflection coefficient was determined experimentally within egg white. Reference numeral 201 shows the prominent resonant frequency of one example of a microwave antenna in a first configuration, where the downward spike at around 2.25 GHz represents the prominent resonant frequency for that antenna configuration. The parameters of the first configuration have a choke length of 10 millimeters, an arm length of 6 millimeters, a radiating portion length of 1 millimeter, a cap base length of 5 millimeters, and a cap tip length of 5 millimeters, for an overall length of 27 millimeters. Reference numeral 202 shows a decrease in the resonant frequency of a different probe in which the radiating portion length of the antenna was increased by 1 millimeter versus the first configuration, while the other parameters remain constant. Reference numeral 203 shows an increase in resonant frequency of a third probe in which the length of the arm is decreased by 1 millimeter versus the first configuration, and reference numeral 204 shows a decrease in resonant frequency versus the original configuration for a fourth probe when the length of the arm is increased by 1 millimeter compared to the first configuration.

Figure 3:
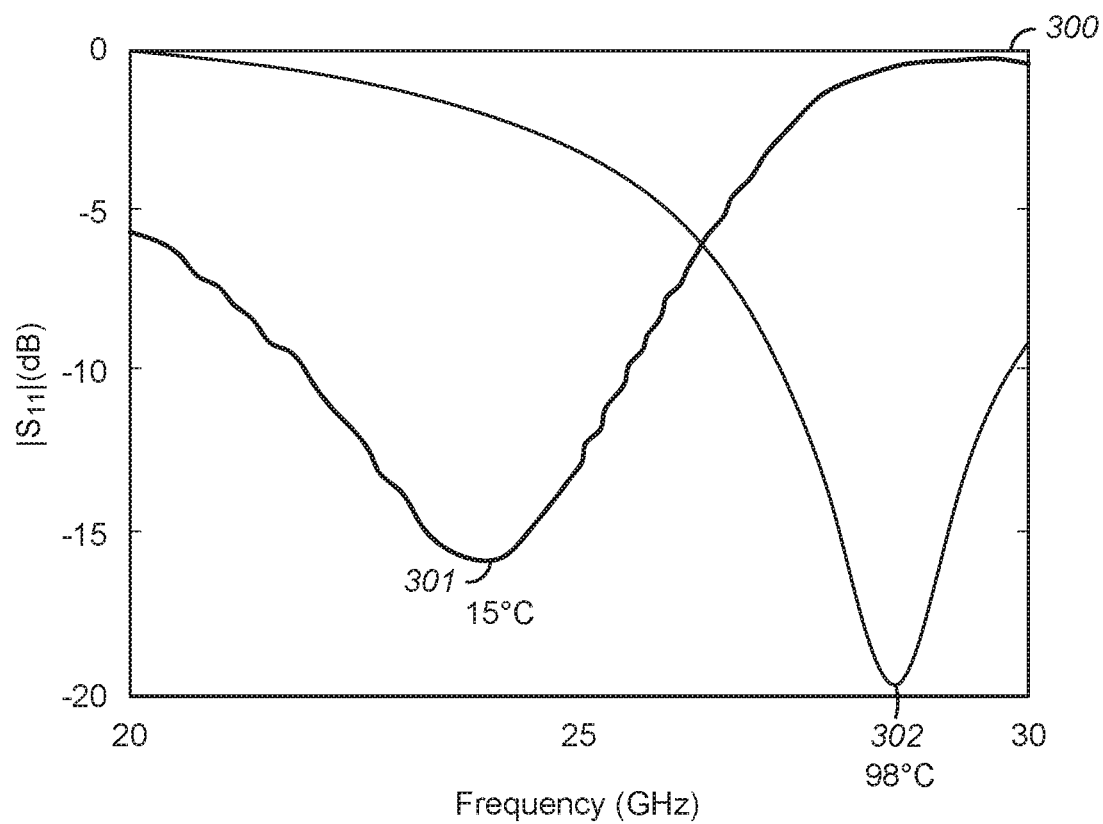
FIG. 3 is a graph showing the temperature dependence of resonant frequency for a microwave ablation antenna.

FIG. 3 shows a second graph 300 demonstrating the change in resonant frequency for a single configuration of a microwave antenna as the temperature of patient tissue surrounding the probe increases. The graph 300 also shows the antenna reflection coefficient, $|S_{11}|$ in decibels plotted against frequency in Gigahertz. The graph 300 is from Erin Coleback and Erdem Topsakal, *Ultra-Wideband Microwave Ablation Therapy (UMAT)*, IEEE MTT-S International Microwave Symposium Digest (2013), which is hereby incorporated by reference herein in its entirety. Plot 301 shows a prominent resonance frequency for the antenna when the surrounding patient tissue is at temperature of 15 degrees Celsius. Plot 302 shows an increase in the prominent resonance frequency for the same antenna when the surrounding patient tissue is at a temperature of 98 degrees Celsius. In the example of FIG. 3, at 15 degrees Celsius, the resonant frequency of the antenna matches the liver tissue at about 2.45 GHz with 97.5% energy transmitted to tissue and 2.5% reflected. However, at 98.9 degrees Celsius, the resonant frequency of the antenna shifts up to about 2.8 GHz and only a small portion, about 20 percent of the energy, is transmitted into tissue.

As demonstrated in the graphs shown in FIGS. 2 and 3, the resonant frequency of a microwave ablation antenna is both temperature dependent and dependent on the dimensions of structures of the antenna. The resonant frequency is also dependent on the qualities of the patient tissue. When the parameters of the antenna are fixed, the antenna has a higher amplitude of radiation at the resonant frequency of the antenna. Since the dielectric properties of the tissue change when the tissue is heated to different temperature, a fixed antenna can only match the tissue resonant frequency at a given frequency and temperature. A fixed antenna loses efficiency as tissue heats up.

The change in tissue temperature due to heating during the ablation procedure causes the resonant frequency of the antenna to change, which creates a mismatch between the antenna resonant frequency and the desired working frequency (915 MHz or 2.45 GHz). The technology herein describes an antenna design with variable antenna parameters. This variable parameter antenna has a wider range of resonance frequencies; although the amplitude of radiation of the disclosed variable parameter antenna is decreased versus a fixed parameter antenna, the resonant frequency of the variable parameter antenna coincides with the working frequency (915 MHz or 2.45 GHz) over a wider range of temperatures so it can effectively radiate microwave energy into tissue. This is more suitable for different tissue ablation scenarios and results in better ablation performance.

The disclosed antenna with variable parameters acts as multiple antennas each with different resonant frequencies connected in parallel. The antenna with variable parameters has a part of the antenna with a resonant frequency at the working frequency (915 MHz or 2.45 GHz) and transmits the energy with a sufficiently high energy amplitude to work with different tissue types and at different temperatures.

In the various implementations of the variable length antenna, the length of the radiating portion varies around the circumference of the coaxial cable. For example, the length of the radiating portion can vary from 0.5 mm to 1.5 mm The antenna behaves as if there were multiple antennas with different resonant frequencies ranging from 2 GHz to 3 GHz connected in parallel. In this way, there is always a part of the antenna resonant at 2.45 GHz even when the tissue properties change due to different tissue types and different tissue temperatures. As will be discussed below, the variable length parameters can be discrete or continuous.

Microwave Ablation System

Figure 4:
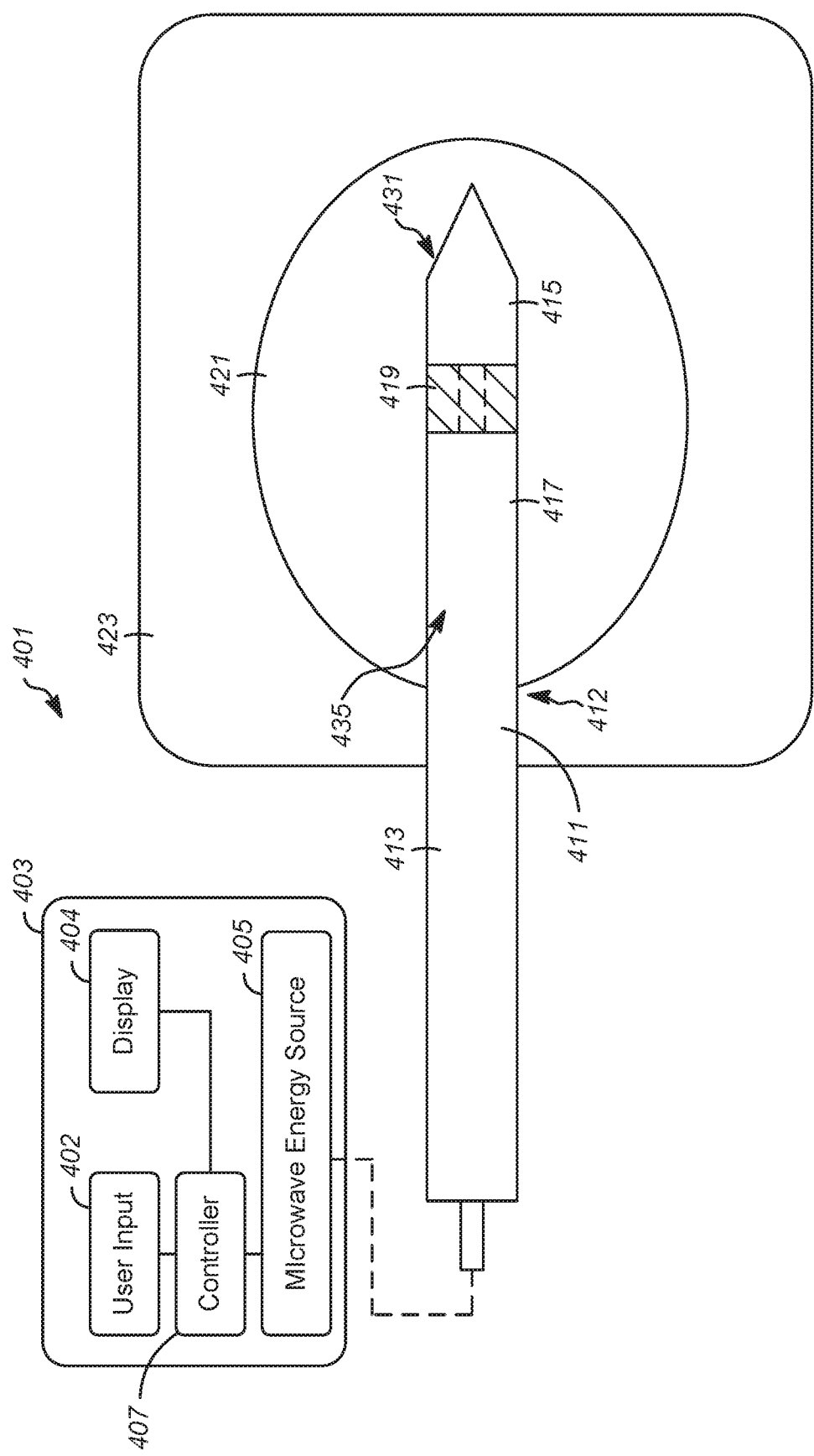
FIG. 4 is a schematic view of a microwave ablation system including a microwave ablation probe according to some examples.

FIG. 4 is a schematic view of a microwave ablation system according to some examples. The system 401 includes a microwave ablation control unit 403, which includes a microwave energy source 405 that delivers microwave energy to an ablation probe 411. The microwave ablation control unit 403 also includes a controller 407, which can be a microprocessor that controls the microwave energy source, a user input 402, and a display 404, allowing a physician or other medical professional to monitor and interact with the control unit 403.

An available microwave ablation generator is the Sairem GMS solid state generator, operating at 200 W and 2450 MHz, manufactured by Sairem, of Neyron, France. Alternatively, the Emblation Microwave MSYS245 Medical System, operating at 100 W and 2450 MHz, manufactured by Emblation Microwave, an Emblation Limited Company, of Scotland, UK can be used. These commercial systems and any combination can be used to implement the system described herein.

Microwave Ablation Probe

The microwave ablation probe includes a probe body 412 with a radiation window 419 at a distal portion 431 of the ablation probe 411. The elongate probe body 412 can include a cannula 413 that is provided in a variety of lengths. The length of the probe body 412 is much larger than its diameter. For example, the length may be 10 times the diameter or more, 50 times the diameter or more, 100 times the diameter or more, or 200 times the diameter or more. The length may be at least 5 centimeters or at least 10 centimeters.

The probe 411 has a cap tip 415 at a distal portion 431 of the probe 411 that is configured to be inserted into patient tissue 423. In some examples, the cap tip 415 has a tissue-piercing tip configured for percutaneous entry into patient tissue 423. The ablation probe 411 has a shielded portion 417 that prevents microwave energy from entering patient tissue along the proximal portion 435 of the probe body 412, and a radiation window 419 that is transparent to microwave energy, allowing microwave energy to be transmitted into the patient tissue 423 to create the lesion 421. The radiation window 419 is at least partially transparent to electromagnetic radiation emitted in the microwave range of the electromagnetic spectrum with a frequency on the order of about 300 megahertz to 300 gigahertz. The length of the radiation window 419 is based on the particular antenna used in the microwave ablation probe 411. In some examples, the length of the radiation window 419 is at least about 7 millimeters, at least about 10 millimeters, or at least about 13 millimeters. In some examples, the length is at most about 30 millimeters, or at most about 20 millimeters. In one example, the length is about 15 millimeters.

Variable Arm Length and Radiating Portion Length

Figure 5:
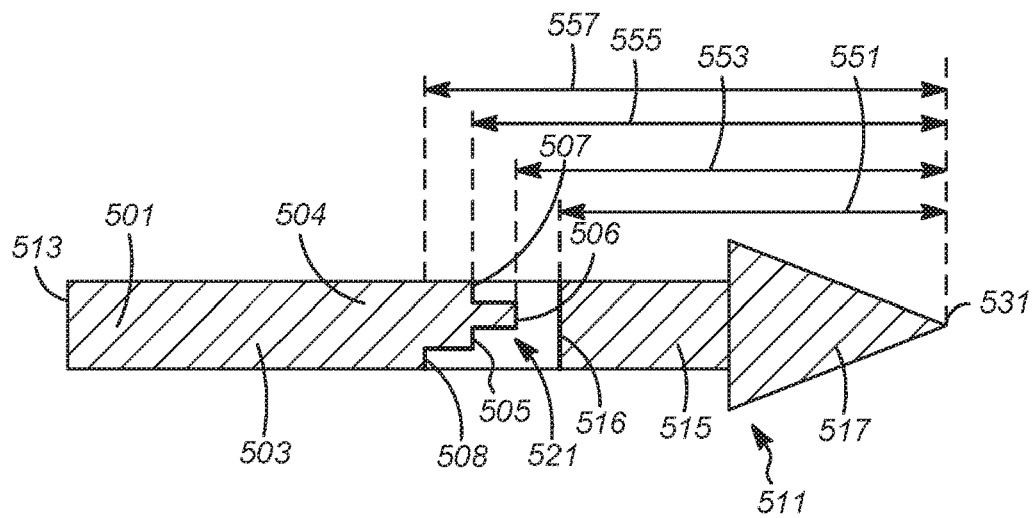
FIG. 5 is a side view of a microwave ablation antenna having variable parameters according to some examples.
Figure 6:
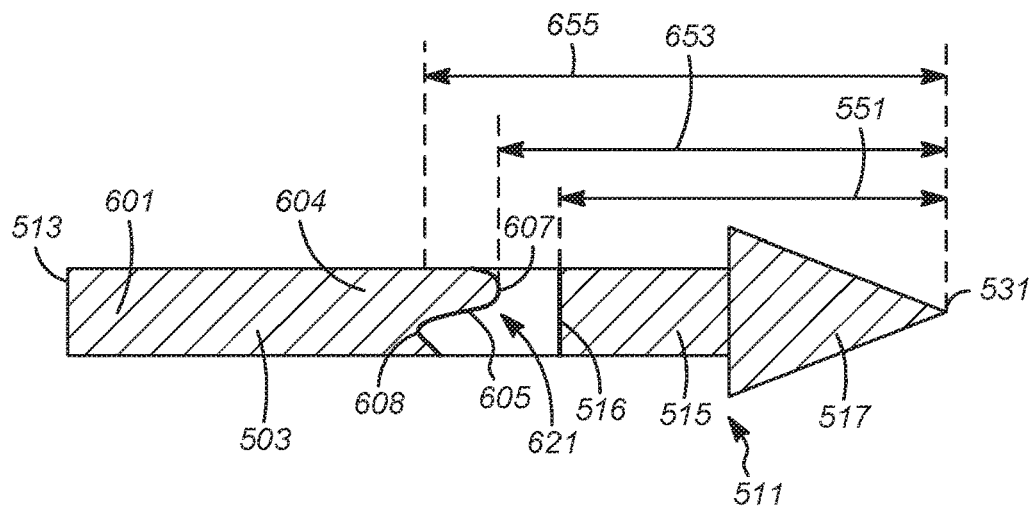
FIG. 6 is a side view of a microwave ablation antenna having variable parameters according to some examples.
Figure 7:
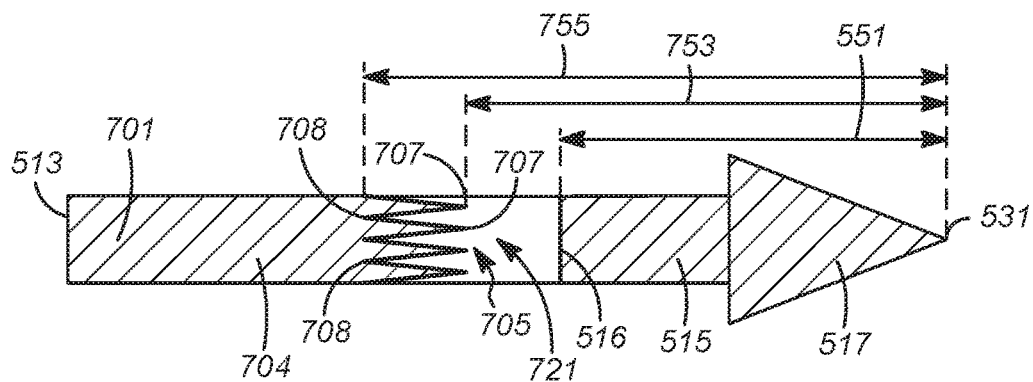
FIG. 7 is a side view of a microwave ablation antenna having variable parameters according to some examples.
Figure 8:
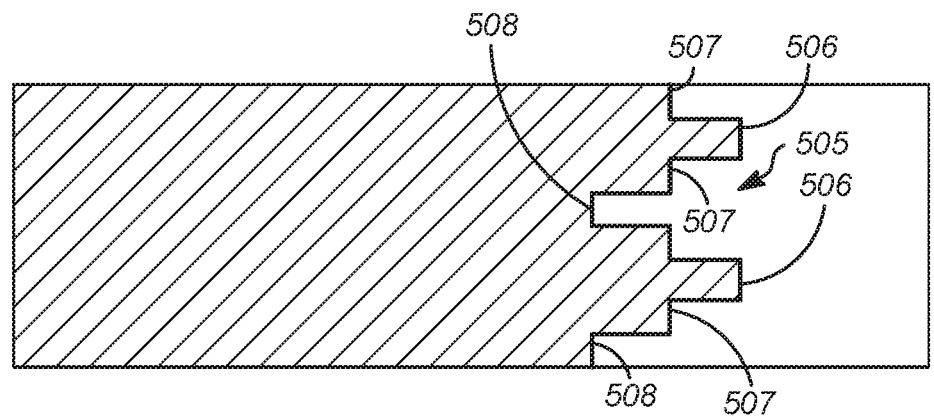
FIG. 8 is an unrolled cylindrical view of the antenna of FIG. 5.
Figure 9:
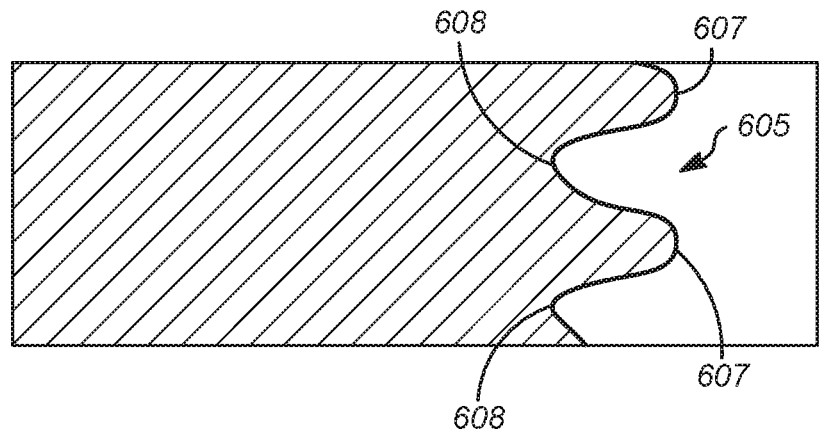
FIG. 9 is an unrolled cylindrical view of the antenna of FIG. 6.
Figure 10:
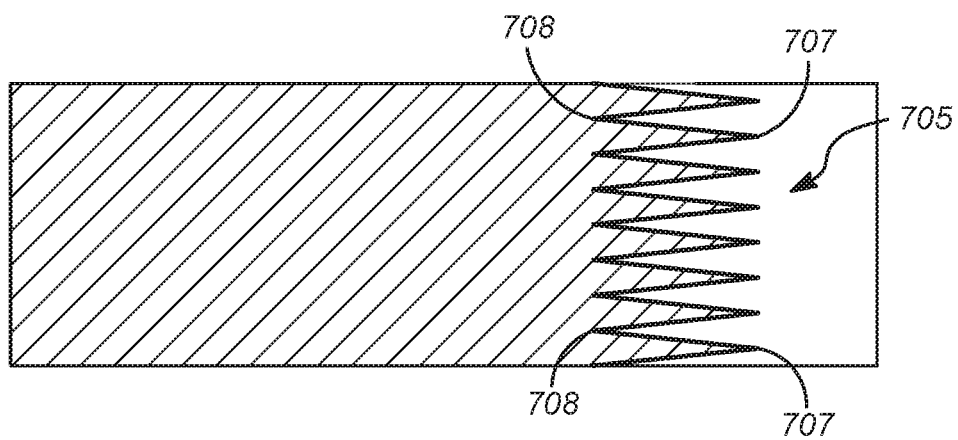
FIG. 10 is an unrolled cylindrical view of the antenna of FIG. 7.

FIGS. 5-7 are side views of variable length antennas according to some examples. FIGS. 8-10 show unwrapped cylinder views of the variable length antennas in FIGS. 5-7. For purposes of illustration, a side view of a distal portion of the coaxial cable antenna and the cap that extends beyond a cannula is shown in FIGS. 5-7. The distal portion of the coaxial cable is shown down from the distal end to the boundary 513 where the coaxial cable meets the cannula distal end or end of the choke length. The cannula and dielectric material that will surround the coaxial cable in the probe are omitted from FIGS. 5-7 so that dimensions of the outer conductor, cap, and radiating portion can be described. The inner conductor of the coaxial cable is not visible in the side views of FIGS. 5-7 as it is behind the dielectric material of the radiating window portion. In the example of FIGS. 5-7, the cap length, including the cap base length and the cap tip length remain constant. The arm length and the radiating portion length are variable in these examples, because of variance of the distal boundary of the outer conductor.

In FIG. 5, the variance in antenna shape is a rectangular, stepped shape in which adjacent discrete sections of the outer conductor are at different distances from the probe distal end. In FIG. 6, the variance in antenna shape is a sinusoidal wave shape. In FIG. 7, the variance in antenna shape is a saw tooth shape. These shapes can be formed, for example, by laser cutting or die cutting of the outer conductor. In some examples, the outer conductor of the antenna is copper, and chemical etching is used with a mask to form the variable antenna shape.

In FIG. 5, a coaxial antenna 501 includes an outer conductor 503 having a distal boundary 505. An arm 504 extends from the end 513 of the cannula to the distal boundary 505 of the outer conductor 503. The proximal boundary of the arm 504 is the end 513 of the cannula. The arm proximal boundary is the axial location of the cannula distal end on the outer conductor 503. A cap 511 includes a cap base 515 and a cap tip 517. The cap base 515 has a proximal boundary 516. The radiating portion 521 is defined between the distal boundary 505 of the outer conductor 503 and the proximal boundary 516 of the cap base 515. As described herein, the cap 511 has a cap length 551 defined between the probe distal end 531 and the cap proximal boundary 516. In the example of FIG. 5, the cap proximal boundary 516 has a constant, uniform distance from the probe distal end 531. The outer conductor distal boundary 505 comprises a plurality of discrete sections that are at different distances from the probe distal end 531. FIG. 8 shows an unwrapped cylinder view of the example of FIG. 5; as can be seen in FIG. 8, a repeating stepped pattern of the distal boundary 505 is provided around the circumference of the coaxial antenna 501. The distal boundary of the arm 504 is the distal boundary 505 of the outer conductor 503. The distal boundary 505 of the outer conductor has a first distance 553 from the probe distal end 531, defined between the probe distal end 531 and a first portion 506 of the outer conductor distal boundary 505. The distal boundary 505 of the outer conductor has a second distance 555 from the probe distal end 531, defined between the probe distal end 531 and a second portion 507 of the outer conductor distal boundary 505. The outer conductor distal boundary 505 has a third distance 557 defined between the probe distal end 531 and a third portion 508 of the outer conductor distal boundary 505. The variations between the distances 553, 555, and 557 create a distal boundary 505 that has a stepped shape. The arm 504 has a variable length, as measured between a distal boundary 505 of the arm 504 and the arm proximal boundary 513. The radiating portion 521 has different lengths at each of the different portions 506, 507, and 508 of the distal boundary. Each of the portions 506, 507, and 508 create different resonant frequencies for the antenna 501.

FIG. 6 shows the coaxial antenna 601 having a probe distal end 531, and a cap 511 comprising a cap base 515 and a cap tip 517. The proximal boundary 516 of the cap 511 remains at a constant, uniform distance from the probe distal end 531. The arm 604 of the antenna 601 includes a distal boundary 605 that is continuously variable. The distal boundary 605 has a first length 653 from the probe distal end 531 defined between the probe distal end 531 and a first portion 607 of the distal boundary 605. The distal boundary 605 has a second length 655 from the probe distal end 531 defined between the probe distal end 531 and a second portion 608 of the distal boundary 605. In the example of FIG. 6, the distal boundary 605 has a continuously variable length in relation to the probe distal end 531, rather than discrete sections at different lengths. Stated differently, the example of FIG. 6 provides a continuously variable length of arm 604. The arm 604 has a variable, as measured between the arm distal boundary 605 and the arm proximal boundary 513. FIG. 9 shows an unwrapped cylindrical view of the example of FIG. 6. The distal boundary 605 has a sinusoidal pattern between the distal boundary portions 607 and 608. The radiating portion 621 has different lengths at each of the different portions of the distal boundary 605. The sinusoidal shape of the distal boundary 605 creates different resonant frequencies for the antenna 601. FIG. 7 shows the coaxial antenna 701 having a probe distal end 531 and a cap 511 comprising a cap base 515 and a cap tip 517. The proximal boundary 516 of the cap 511 remains at a constant, uniform distance from the probe distal end 531. The arm 704 of the antenna 701 includes a distal boundary 705 that is continuously variable in its length and distance from distal end 531. The distal boundary 705 has a first length 753 from the probe distal end 531, defined between the probe distal end 531 and a first portion 707 of the distal boundary 705. The distal boundary 705 has a second length 755 from the probe distal end 531, defined between the probe distal end 531 and a second portion 708 of the distal boundary 705. In the example of FIG. 7, the distal boundary 705 of the arm 704 also has a variable length in relation to the arm proximal boundary 513. FIG. 10 shows an unwrapped cylindrical view of the example of FIG. 7. The distal boundary 705 creates a saw tooth pattern between the distal boundary portions 707 and 708. The radiating portion 721 has different lengths at each of the different portions of the distal boundary 705.

Variable Cap Length and Radiating Portion Length

Figure 11:
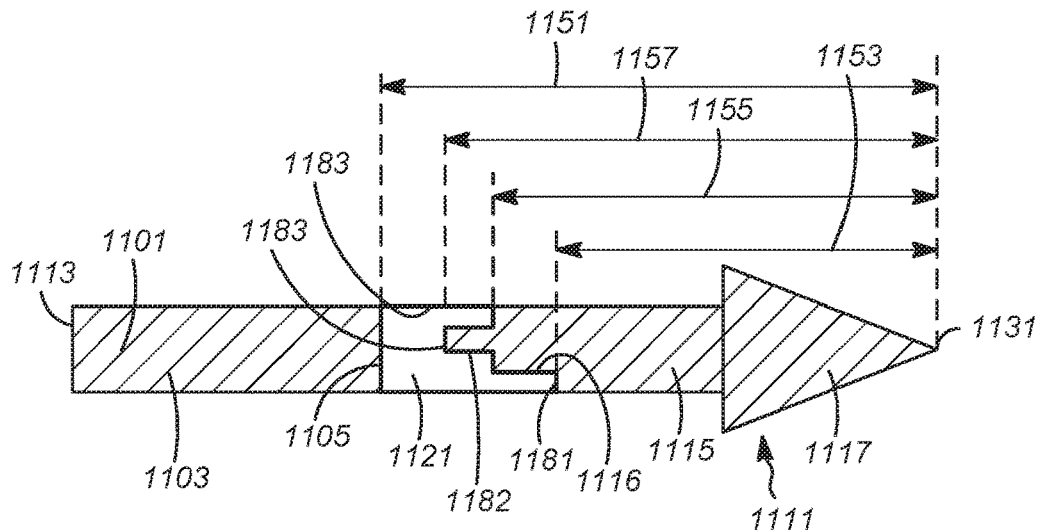
FIG. 11 is a side view of a microwave ablation antenna having variable parameters according to some examples
Figure 12:
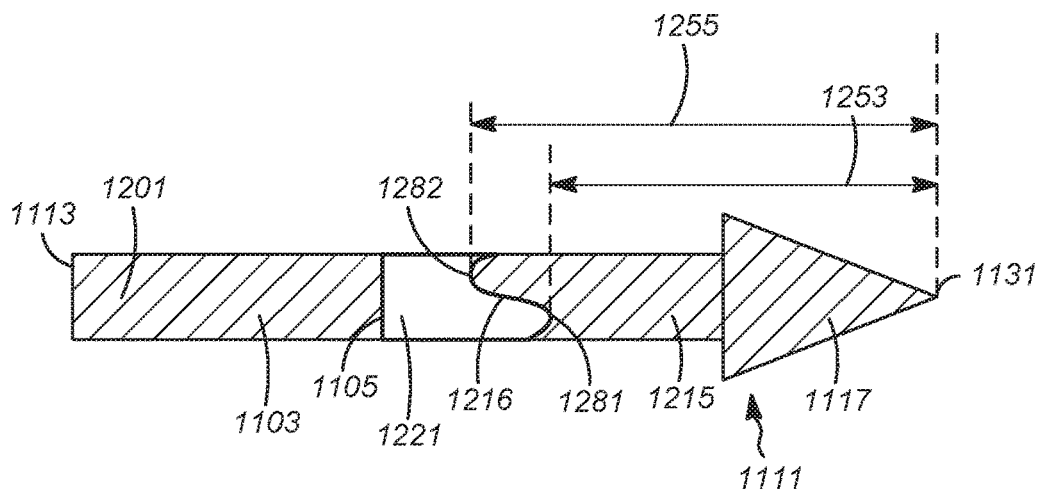
FIG. 12 is a side view of a microwave ablation antenna having variable parameters according to some examples
Figure 13:
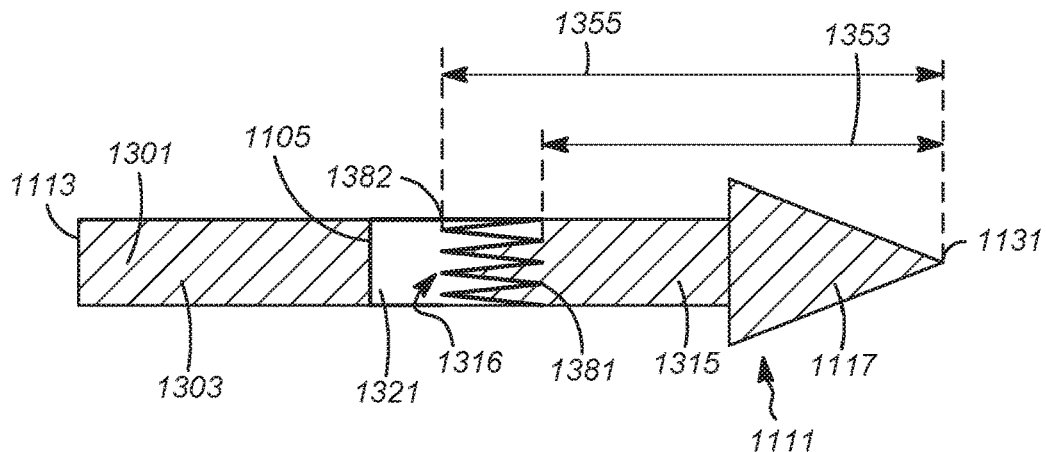
FIG. 13 is a side view of a microwave ablation antenna having variable parameters according to some examples

FIGS. 11-13 show alternative examples of an antenna having portions with different dimensions from neighboring portions. For purposes of illustration, only the coaxial cable antenna and the cap are shown in FIGS. 11-13, distal to the proximal boundary 1113 of the arm, where the cannula ends, similar to the portion illustrated in FIGS. 5-7. In the example of FIGS. 11-13, the arm length and cap tip length remain constant, while the radiating portion length and the cap base length are each variable. Because the cap base length is variable, the cap length is also variable.

In FIG. 11, coaxial antenna 1101 includes an outer conductor 1103 having a distal boundary 1105. The outer conductor 1103 has a distal boundary 1105 that has a constant length 1151 between the distal boundary 1105 and the probe distal end 1131. Also, the arm length of the antenna 1101, between a proximal boundary 1113 of the arm and the distal boundary 1105 of the arm, remains constant. Cap base 1115 has a proximal boundary 1116 that provides a variable cap base length. The radiating portion 1121 is defined between the distal boundary 1105 of the outer conductor 1103 and the proximal boundary 1116 of the cap base 1115. The variable cap base length causes the radiating portion 1121 to have a variable length. The cap base length includes a first length 1153 defined between the probe distal end 1131 and a first portion of the cap base proximal boundary 1181. The cap base length includes a second length 1155 defined between the probe distal end 1131 and a second portion of the cap base proximal boundary 1182. The cap base length includes a third length 1157 defined between the probe distal end 1131 and a third portion of the cap base proximal boundary 1183. The variations between the lengths of proximal boundary portions 1181, 1182, and 1183 create a proximal boundary 1116 of the cap base 1115 that has a stepped shape. The radiating portion 1121 has different lengths at each of the different portions 1181, 1182, and 1183 of the proximal boundary. Each of the portions 1181, 1182, and 1183 create different resonant frequencies for the antenna 1101.

FIG. 12 shows the antenna 1201 with the cap base 1215 having a sinusoidal proximal boundary 1216. The sinusoidal proximal boundary 1216 comprises a first cap length 1253 between a first portion 1281 of the proximal boundary and the probe distal end 1131, and a second length 1255 between the probe distal end 1131 and a second portion 1282 of the proximal boundary. In between the first portion 1281 and the second portion 1282, the proximal boundary 1216 is continuously variable, providing a continuously variable cap length. The variable cap base length causes the radiating portion 1221 to have a variable length.

FIG. 13 shows the antenna 1301 including an outer conductor 1303 and with the cap base 1315 having a saw tooth proximal boundary 1316. The saw tooth proximal boundary 1316 creates a first cap length 1353 between the probe distal end 1131 and a first portion of the proximal boundary 1381, and a second cap length 1355 between the probe distal end 1131 and a second portion of the proximal boundary 1382. The variable cap base length causes the radiating portion 1321 to have a variable length. The saw tooth shape of the proximal boundary 1316 creates a continuously variable cap length, creating a variety of different resonant frequencies for the antenna 1301.

Variable Arm Length, Cap Length, and Radiating Portion Length

Figure 14:
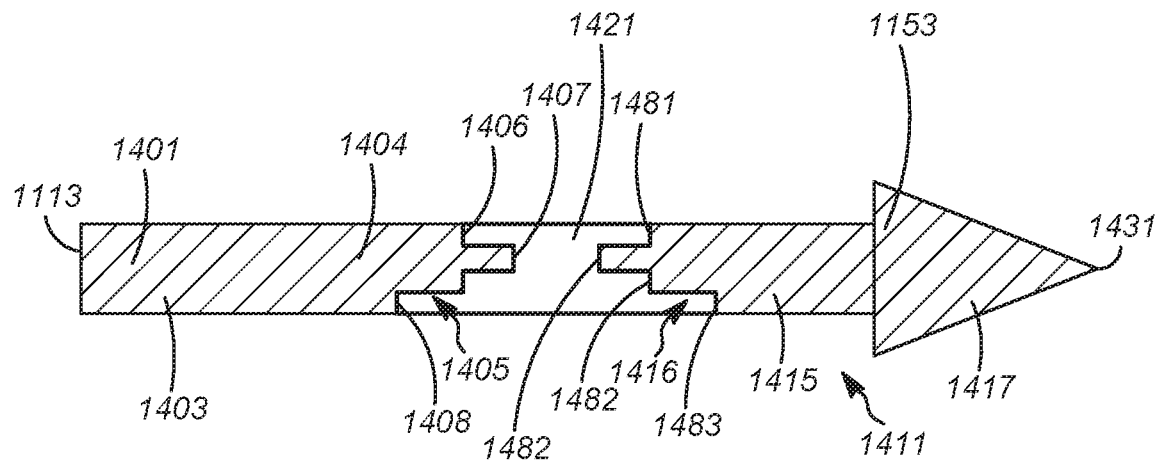
FIG. 14 is a side view of a microwave ablation antenna having variable parameters according to some examples
Figure 15:
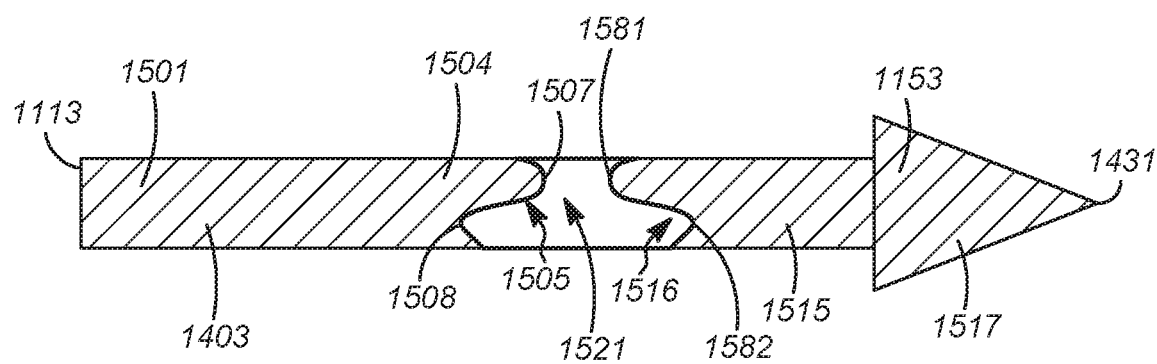
FIG. 15 is a side view of a microwave ablation antenna having variable parameters according to some examples
Figure 16:
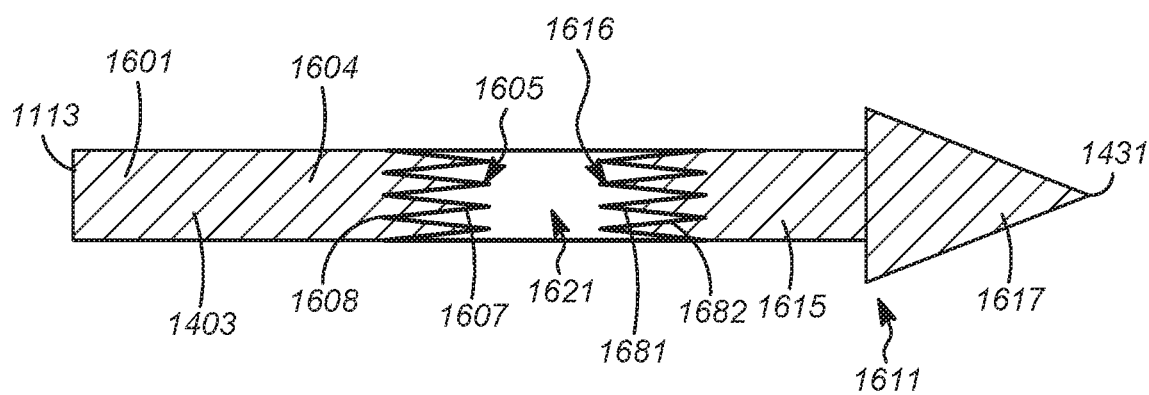
FIG. 16 is a side view of a microwave ablation antenna having variable parameters according to some examples

FIGS. 14-16 are schematic views of variable length antennas according to some examples. For purposes of illustration, only the coaxial cable antenna and the cap are shown in FIGS. 14-16. For purposes of illustration, only the coaxial cable antenna and the cap are shown in FIGS. 14-16, distal to a proximal boundary 1113 of the arm, where the cannula ends, similar to the portion illustrated in FIGS. 5-7 and FIGS. 11-13. In the example of FIGS. 14-16, the arm length, the radiating portion length, and the cap length each include portions that vary in length compared to the distal end of the probe and compared to neighboring portions. In the example of FIGS. 14-16, the cap includes a cap base and a cap tip. The cap tip has a constant length, and the cap base has a variable length.

In FIG. 14, the coaxial antenna 1401 includes an outer conductor 1403 that defines an arm 1404. The outer conductor 1403 has a distal boundary 1405 that has different segments 1406, 1407, and 1408 that each is located a different length from the probe distal end 1431. The A cap 1411 includes a cape base 1415 and a cap tip 1417. Additionally, the cap base 1415 has a proximal boundary 1416 that is made up of different segments 1481, 1482, 1483 that each have different lengths from the probe distal end 1431. The radiating portion 1421 has a variable length that is defined between the distal boundary 1405 of the outer conductor 1403 and the proximal boundary 1416 of the cap base 1415. The distal boundary 1405 of the outer conductor 1403 and the proximal boundary 1416 of the cap base 1415 create a variable length for the radiating portion 1421. The minimum length of the radiating portion 1421 is situated between the distal boundary portion 1407 of the arm 1404 and the proximal boundary portion 1482 of the cap base 1415. The maximum length of the radiating portion 1421 is situated between the distal boundary portion 1408 of the arm 1404 and the proximal boundary portion 1483 of the cap base 1415. The variable distal boundary 1405 creates a variable arm length, where the outer conductor distal boundary varies in distance from the probe distal end 1431. The variable proximal boundary 1416 creates a variable cap length, where the cap base proximal boundary 1416 varies in distance from the probe distal end 1431. These variable lengths of the arm 1404, the radiating portion 1421, and the cap 1411 create a range of different resonant frequencies for the antenna 1401.

Figure 23:
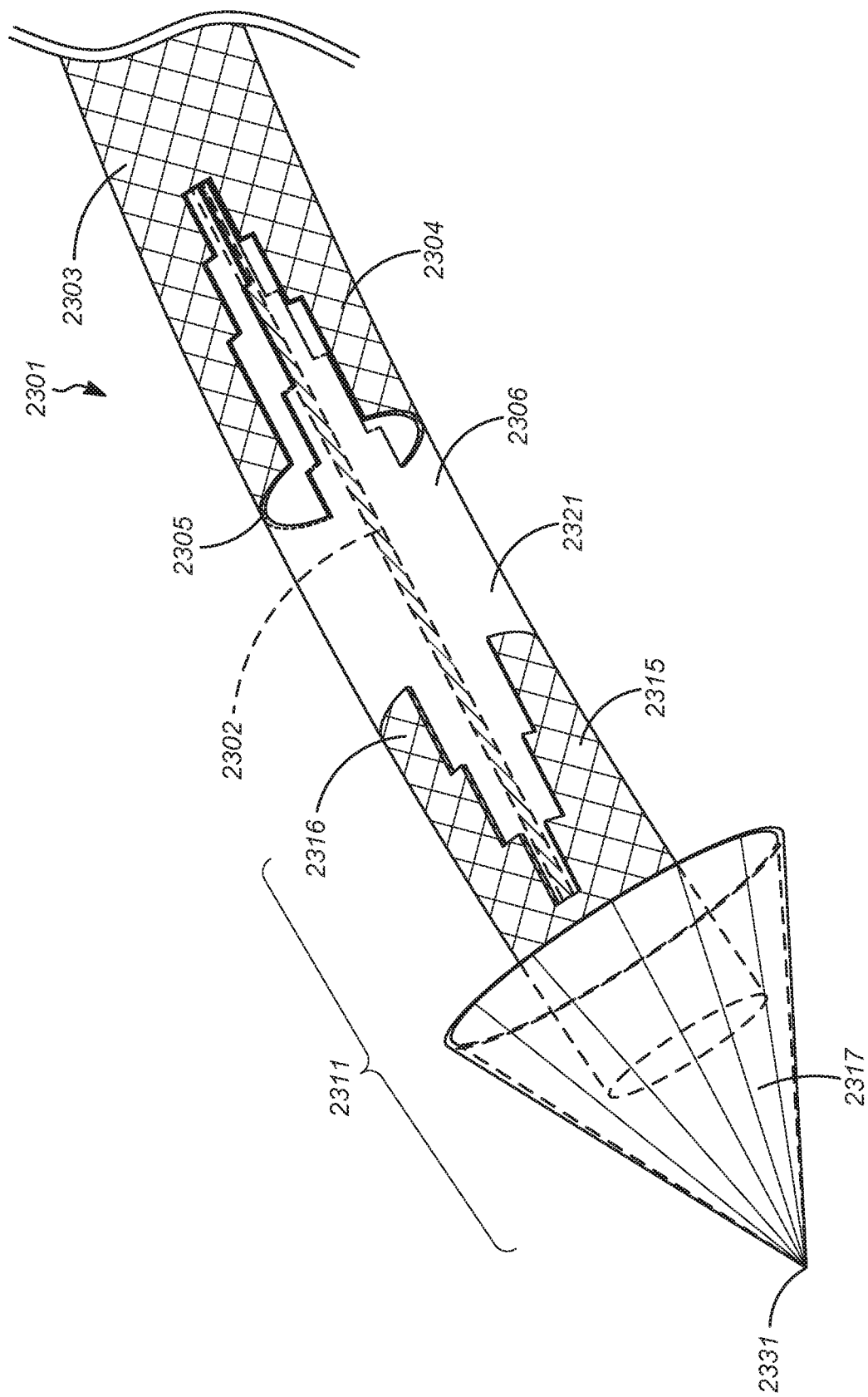
FIG. 23 is a cutaway perspective view of a microwave antenna having variable parameters according to some examples.

FIG. 23 is a partially cutaway perspective view of an antenna 2301 for a microwave ablation probe. Antenna 2301 is similar to antenna 1401 because both the arm length and cap length vary in stepped segments. Antenna 2301 has different dimensions and proportions of the stepped segments compared to antenna 1401 of FIG. 14. The perspective view of FIG. 23 provides additional insight into the structure of an antenna with variable dimensions for the arm and cap base. A cannula is not shown in FIG. 23.

The antenna 2301 has a variable arm length and a variable cap length, and as a result, a variable radiating portion length. The antenna 2301 is a coaxial antenna having a center conductor 2302 and an outer conductor 2303. A dielectric material 2306 separates the center conductor 2302 and the outer conductor 2303. The outer conductor 2303 forms an arm 2304. The outer conductor 2303 has a distal boundary 2305 that varies in distance from the probe distal end 2331. The antenna 2301 further includes a cap base 2315 having a proximal boundary 2316 that has a variable distance from the probe distal end 2331. The variable proximal boundary 2316 provides the cap 2311, which includes a cap tip 2317 and the cap base 2315, with a variable length. A radiating portion 2321 is defined between the distal boundary 2305 and the proximal boundary 2316.

In FIG. 15, the coaxial antenna 1501 includes the outer conductor 1403 that defines an arm 1504. The arm 1504 has a sinusoidal distal boundary 1505. The coaxial antenna 1501 further includes a cap base 1515 that has a sinusoidal proximal boundary 1516. The antenna 1501 also includes a cap tip 1517. The distal boundary 1505 of the arm 1504 includes a first distal boundary portion 1507 and a second distal boundary portion 1508. The proximal boundary 1516 of the cap base 1515 includes a first proximal boundary portion 1581 and a second proximal boundary portion 1582. The distal boundary 1505 and the proximal boundary 1516 create a variable length for the radiating portion 1521. The radiating portion 1521 has a minimum length between the first proximal portion 1581 of the cap base 1515, and the first distal portion 1507 of the arm 1504. The radiating portion 1521 has a maximum length between the second proximal portion 1582 of the cap base 1515 and the second distal portion 1508 of the arm 1504. The variable distal boundary 1505 creates a variable arm length, where the outer conductor distal boundary varies in distance from the probe distal ends 1431. The variable proximal boundary 1516 creates a variable cap length, where the cap proximal boundary varies in distance from the probe distal end 1431. These variable lengths of the arm 1504, the radiating portion 1521, and the cap create a range of different resonant frequencies for the antenna 1501.

In FIG. 16, the coaxial antenna 1601 includes the outer conductor 1403 that defines an arm 1604. The arm 1604 has a saw tooth distal boundary 1605. The coaxial antenna 1601 further includes a cap 1611 which has a cap base 1615 and a cap tip 1617. The cap base 1615 has a saw tooth proximal boundary 1616. The distal boundary 1605 of the arm 1604 includes a first distal boundary portion 1607 and a second distal boundary portion 1608. The proximal boundary 1616 of the cap base 1615 includes a first proximal boundary portion 1681 and a second proximal boundary portion 1682. The distal boundary 1605 and the proximal boundary 1616 create a variable length for the radiating portion 1621. The radiating portion 1621 has a minimum length between the first proximal portion 1681 of the cap base 1615, and the first distal portion 1607 of the arm 1604. The radiating portion 1621 has a maximum length between the second proximal portion 1682 of the cap base 1615 and the second distal portion 1608 of the arm 1604. The variable distal boundary 1605 creates a variable arm length, where the outer conductor distal boundary varies in distance from the probe distal ends 1431. The variable proximal boundary 1616 creates a variable cap length, where the cap proximal boundary varies in distance from the probe distal end 1431. These variable lengths of the arm 1604, the radiating portion 1621, and the cap 1611 create a range of different resonant frequencies for the antenna 1601.

Alternative Antenna Types

FIGS. 17-21 show cross-sectional drawings of different coaxial microwave antenna types that can be used to create variable length antennas according to the technology disclosed herein. FIGS. 17-21 show a distal end portion of a coaxial cable that makes up part of each antenna, including a center conductor, an outer conductor, and an insulation layer in between the inner and outer conductor.

Figure 17:
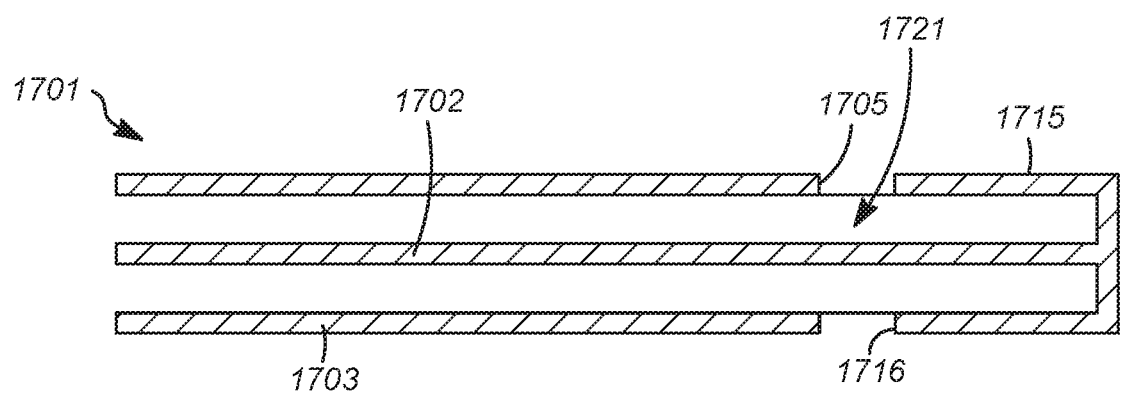
FIG. 17 is a cross-sectional view of a slot microwave antenna.

In FIG. 17, the microwave antenna 1701 is a slot antenna having a center conductor 1702 and an outer conductor 1703. In some examples, a distal boundary 1705 of the outer conductor 1703 can be configured to have a variable distance from the distal end of a microwave ablation probe. In some examples, a proximal boundary 1716 of a cap base 1715 can be configured to have a variable distance from the distal end of a microwave ablation probe. In some examples, both the distal boundary 1705 and the proximal boundary 1716 can be configured to have a variable distance from the distal end of a microwave ablation probe. These variable lengths allow the length of a radiating portion 1721 situated between the distal boundary 1705 and of the proximal boundary 1716 to have a variable width, providing the antenna 1701 with a range of different resonant frequencies.

Figure 18:
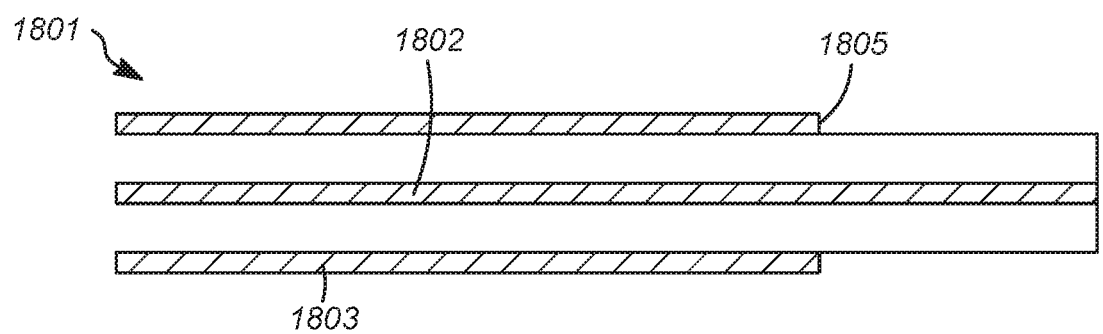
FIG. 18 is a cross-sectional view of a monopole microwave antenna.

In FIG. 18, the microwave antenna 1801 has a center conductor 1802 and an outer conductor 1803. In the example of FIG. 18, the microwave antenna 1801 is a monopole antenna. A distal boundary 1805 of the outer conductor 1803 can be configured to have a variable distance from the end of a microwave ablation probe, providing the antenna 1801 with a variable arm length, and providing the antenna 1801 with a range of different resonant frequencies.

Figure 19:
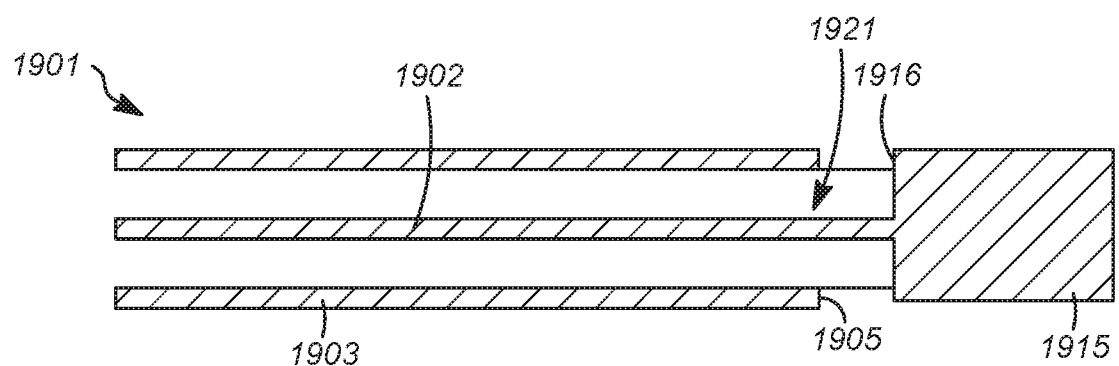
FIG. 19 is a cross-sectional view of a dipole microwave antenna.

In FIG. 19, the microwave antenna 1901 is a dipole antenna with the center conductor 1902 and an outer conductor 1903. The antenna 1901 is further provided with a cap 1915. A proximal boundary 1916 of the cap base, a distal boundary 1905 of the outer conductor 1903, or both can be provided with variable lengths from the distal end of microwave ablation probe. These variable lengths allow the length of a radiating portion 1921 situated between the distal boundary 1905 and the proximal boundary 1916 to have a variable width, providing the antenna 1901 with a range of different resonant frequencies.

Figure 20:
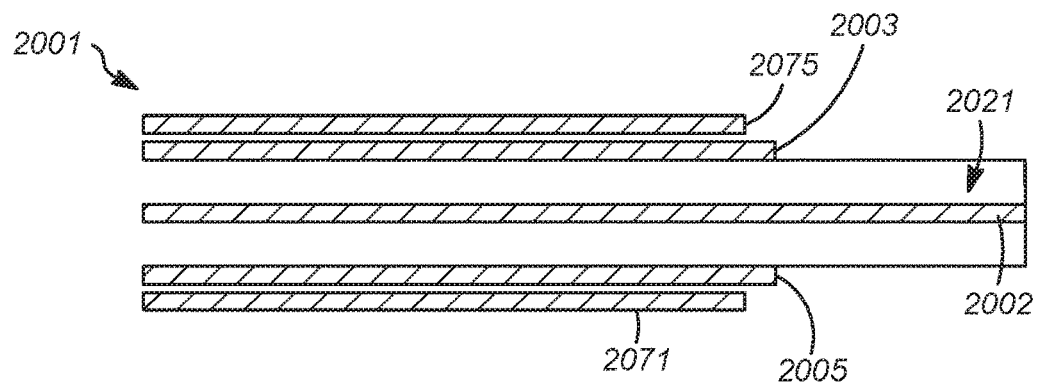
FIG. 20 is a cross-sectional view of a triaxial microwave antenna.

In FIG. 20, a microwave antenna 2001 is a triaxial antenna with a center conductor 2002 and an outer conductor 2003. The triaxial antenna 2001 further has an outer sleeve comprising a shielded portion 2071. A distal boundary 2005 of the outer conductor 2003 can be provided with variable lengths from the probe distal end. Alternatively or in addition, a distal boundary 2075 of the outer shielded portion 2071 can be provided with variable lengths from the probe distal end. The distal boundary 2005 of the outer conductor 2003 determines the length of the radiating portion 2021. The variable distal boundaries provide the antenna 2001 with a range of different resonant frequencies.

Figure 21:
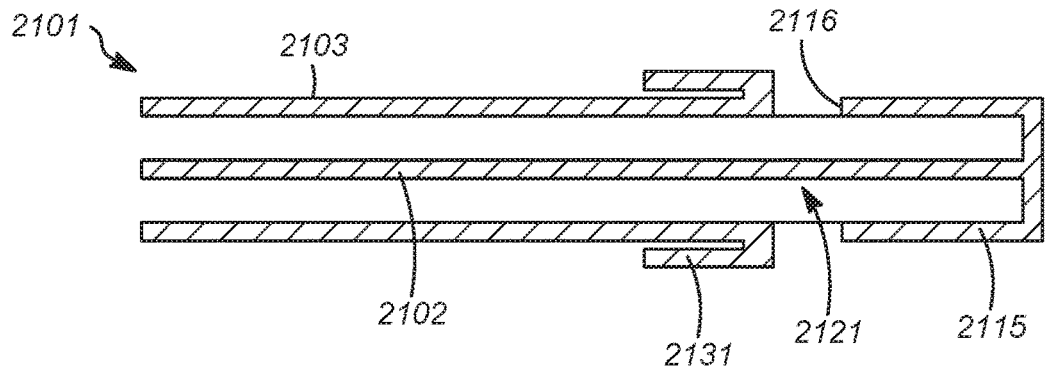
FIG. 21 is a cross-sectional view of a choked microwave antenna.

In FIG. 21, a microwave antenna 2101 is a choked antenna with a coaxial cable having a center conductor 2102, an outer conductor 2103, and a choke 2131. The microwave antenna 2101 further includes a cap base 2115. The cap base 2115 can be provided with a proximal boundary 2116 that has a variable distance from a probe distal end. The radiating portion 2121 of the antenna 2101 has a variable length that is determined between the choke 2131 and the proximal boundary 2116 of the cap base 2115. The variable proximal boundary 2116 provides the microwave antenna 2101 with a range of different resonant frequencies.

Variable Choke Length and Choke Contact

Figure 22:
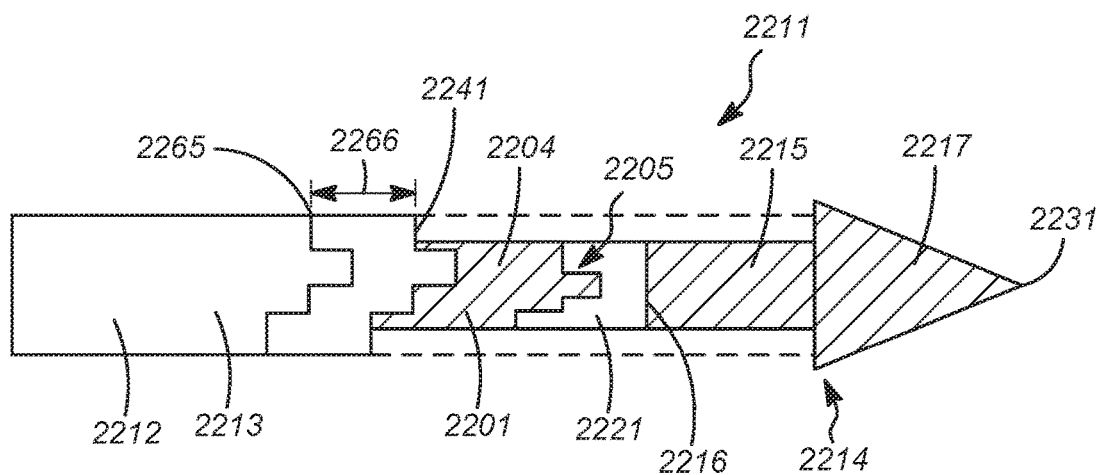
FIG. 22 is a cut-away side view of a microwave ablation probe having variable parameters according to some examples.

FIG. 22 is a side, cutaway view showing an alternative example of a microwave ablation probe having a range of resonant frequencies. The probe 2211 has a coaxial antenna 2201 that includes an arm 2204 and a cap 2214. A cap 2214 includes a cap base 2215 and a cap tip 2217. In the example of FIG. 22, the cap base 2215 has a constant proximal boundary 2216, and the arm 2204 has a variable distal boundary 2205. The radiating portion 2221 has a variable length that varies based on the distal boundary 2205 of the arm 2204. The probe 2211 further includes a shielded portion 2212 that can include a cannula 2213. The cannula 2213 is shown from a side view and extends from a proximal portion of the probe to the distal boundary 2241 of cannula 2213. The distal boundary 2241 of the cannula 2213 can have a variable distance from the probe distal end 2231. The ablation probe 2211 further includes a choke contact 2265 where the cannula 2213 is electrically connected to the underlying outer conductor. A choke length 2266 is defined between the choke contact 2265 and the distal boundary 2241 of the cannula 2213. In some examples, the choke length 2266 is held constant, where the outline of the choke contact 2265 follows the outline of the distal boundary 2241, as shown in FIG. 22. In alternative examples, the choke contact 2265 can have a constant, uniform distance from the probe distal end 2231. In further alternative examples, the cap 2214 can have a varying boundary.

Cooled Antenna Example

Figure 24:
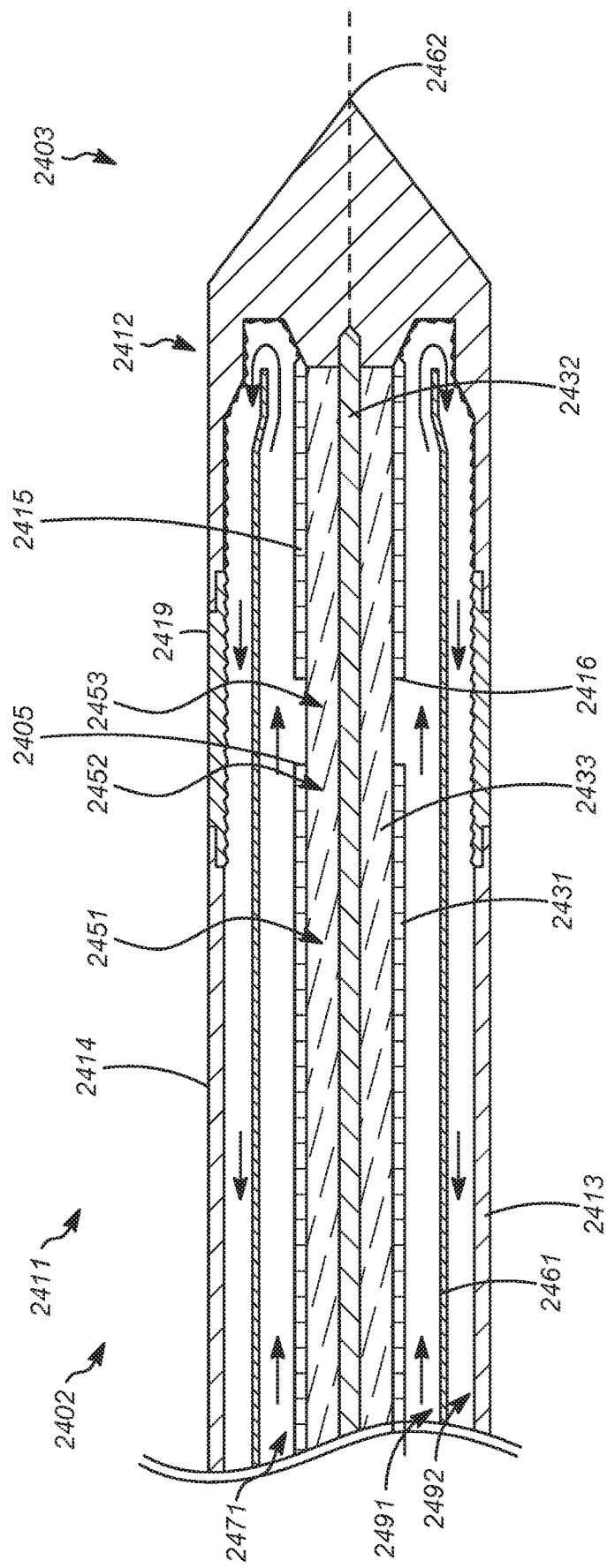
FIG. 24 is a cross-sectional view of an irrigation-cooled microwave ablation probe according to some examples.

FIG. 24 is a cross-sectional view of an irrigation-cooled microwave ablation probe according to some examples. The probe 2411 includes a shielded portion 2414 which includes a cannula 2413. The probe 2411 also includes a coaxial cable 2451 and a liner 2461. The probe body 2412 has a proximal portion 2402 and a distal portion 2403. The coaxial cable 2451 has an inner conductor 2432, an outer conductor 2431, and an insulator 2433 that electrically isolates the inner conductor 2432 and the outer conductor 2431. An antenna 2452 includes a radiating portion 2453 that is aligned with the radiation window 2419 of the probe body 2412.

A cooled fluid is provided along an irrigation path 2471. The irrigation path 2471 includes an inlet path 2491 that receives the cooling fluid from an external portion of the probe 2411, and an outlet path 2492 that channels the fluid out of the probe body 2412 and to a cooling fluid reservoir external to the probe. In some examples, the fluid can be collected in a separate waste fluid reservoir. The cooling fluid cools the coaxial cable 2451 and the probe body 2412. The outer conductor 2431 has a distal boundary 2405 that can have a variable distance from the probe distal end 2462. A cap base 2415 has a proximal boundary 2416 that can have a variable distance from the probe distal end 2462. The radiating portion 2453 has a length that is defined between the distal boundary 2405 of the outer conductor 2431 and the proximal boundary 2416 of the cap base 2415. The radiating portion 2453 can have a variable length. The variable parameters of the antenna 2452 allows the probe 2411 to have a range of different resonant frequencies.

The liner 2461 can be made of an electrically insulating material such as a polymer with a sufficiently high melt temperature to withstand heat created in the system. Some example materials include fluoropolymers or polyamide. A polyamide tubing can have a wall thickness of about 0.001 inch (0.025 mm), less than 0.001 inch (0.025 mm), at least about 0.001 inch (0.025 mm), or at least about 0.001 (0.025 mm) inch and at most about 0.002 inch (0.051 mm) A polymer tubing can have a wall thickness of about 0.003 inch (0.076 mm), at least about 0.003 inch (0.076 mm), or at least about 0.003 inch (0.076 mm) and at most about 0.004 inch (0.102 mm).

In some examples, the inner diameter of the liner 2461 is less than about 0.005 (0.13 mm) inches greater than the outer diameter of the coaxial cable 2451. In some examples, the inner diameter of the cannula 2413 is at least 0.001 inches (0.025 mm) greater than the outer diameter of the liner 2461, and less than 0.005 inches (0.13 mm) greater than the outer diameter of the liner 2461.

In some examples, the flow rate of the cooling fluid through the irrigation path 2471 can be between about 10 ml per minute and 90 ml per minute. In some examples, the flow rate can be between about 30 ml per minute and 50 ml per minute.

Microwave Ablation Methods

A microwave ablation method is provided for a microwave ablation probe having an antenna with variable length parameters. The ablation probe includes a probe body having a shielded portion, a radiation window, and a cap having a cap tip. In some examples, a choke is provided. The probe further includes a coaxial cable antenna having an outer conductor, a center conductor, and a dielectric disposed between the center conductor and the outer conductor. The antenna has a radiating portion which includes the center conductor surrounded by the dielectric, where the outer conductor is not present. The probe has a choke length, and arm length, a radiating portion length, a cap base length, a cap tip length, and a cap length that is defined as the cap base length plus the cap tip link. At least one of the arm length, the radiating portion length, and the cap length are variable around a circumference of the antenna. Around the circumference of the antenna, the different parameter lengths provide the ablation probe with the ability to have a wide band of resonant frequencies.

The method includes inserting the microwave ablation probe into patient tissue. The method further includes ablating the patient tissue by delivering microwave energy through the coaxial cable to the distal end of the microwave antenna. The microwave energy is emitted from the radiating portion of the antenna into patient tissue. The patient tissue has a first temperature before ablation. At least a first portion of the variable length antenna has a resonant frequency in a desired working frequency for the ablation procedure, for example 945 MHz or 2.45 GHz. As the ablation procedure progresses, the patient tissue and the antenna increase in temperature, causing the resonant frequency to change. A second portion of the variable length antenna has a resonant frequency in the desired working frequency for the ablation procedure. At the increased temperature, the first portion of the variable length antenna has a resonant frequency different than the desired working frequency for the procedure.

Materials

The cannula of the probes described herein can be made out of a metal material. In some examples, the cannula is a metal tube, such as a brass tube or a stainless steel hypodermic tube (hypotube). In alternative examples, the cannula can be a polymer tube constructed of materials such as PEBA (polyether block amide), polyimide, polyether ether ketone (PEEK), or polytetrafluoroethylene (PTFE). If the cannula is constructed from a polymer, a separate metallic structure may be provided to serve as a choke, including a choke contact point with the outer conductor and choke length tube or foil attached to the choke contact point, inside the cannula. In one example, the cannula has an inner diameter of about 0.033 inch (0.84 mm), an outer diameter of about 0.039 inch (0.99 mm), and a wall thickness of about 0.006 inch (0.15 mm) In some examples, the cannula has an outer diameter of 0.13 inches (3.4 mm) or less. In some examples, the outer diameter of the cannula is at least about 18 gauge (1.02 millimeters), at least about 17 gauge (1.15 millimeters), or at least about 16 gauge (1.29 millimeters). In some examples, the outer diameter of the cannula 113 is at most about 12 gauge (2.01 millimeters), at most about 13 gauge (1.83 millimeters), or at most about 14 gauge (1.63 millimeters). It will be appreciated that other dimensions are possible for the cannula 113. In some examples, the cannula provides structural integrity to the probe body.

In some examples, the radiation window is a tubular member that forms an extension of the surface of the probe. In some examples, the radiation window can be constructed from fluoropolymers, urethanes, polyether block amides (PEBA), polypropylene, polyethylene, polyamide (nylon), polyimide, polyetherimide (PEI), polysulfone, and polyetheretherketone (PEEK). In some examples, the radiation window can include alumina In some examples, the radiation window is a dielectric layer in between the metal cannula and the outer conductor, and the material of the radiation window extends proximal to the radiation window portion, between the inner diameter of the cannula and the outer diameter of the coaxial cable.

The coaxial cable forming the antenna can be a coaxial cable having an outer diameter of at least about 0.5 millimeters, at least about 0.7 millimeters, at most about 2 millimeters, at most about 5 millimeters, ranging from about 0.5 to about 5 millimeters, or ranging from about 0.7 to about 2 millimeters. The cable can be a coaxial cable having an outer diameter of about 0.864 millimeters, commercially available as part no. UT-034 from Micro-Coax, a Carlisle Interconnect Technologies Company, of Scottsdale, Ariz.

The cap can be constructed from a metal such as brass or stainless steel. In some examples, the cap can be constructed from a ceramic material. In some examples, the cap has a sharp trocar tip with sufficient structural integrity to pierce tissue, allowing the ablation probe to be inserted into the tissue to be ablated. If the cap is made from a metal material, the metal length can be varied to provide the variable length for the antenna.

It should be noted that, as used in this specification and the appended claims, the singular forms include the plural unless the context clearly dictates otherwise. It should also be noted that the term "or" is generally employed in its sense including "and/or" unless the content clearly dictates otherwise. It should also be noted that, as used in this specification and the appended claims, the phrase "configured" describes a system, apparatus, or other structure that is constructed or configured to perform a particular task or adopt a particular configuration. The phrase "configured" can be used interchangeably with other similar phrases such as arranged and configured, constructed and arranged, constructed, manufactured and arranged, and the like.

All publications and patent applications referenced in this specification are herein incorporated by reference in their entirety.

The disclosed technology has been described with reference to various specific and preferred embodiments and techniques. However, it should be understood that many variations and modifications may be made while remaining within the spirit and scope of the technology.

The invention claimed is:

1. A microwave ablation probe comprising:
 a probe body comprising a shielded portion and a radiation window that is at least partially transparent to microwave energy;
 a coaxial cable within the probe body comprising:
  a center conductor,
  a dielectric material surrounding the center conductor of the cable, and
  an outer conductor having an outer conductor distal boundary,
  wherein the center conductor comprises a radiating portion that extends beyond a distal boundary of the outer conductor, wherein the radiating portion is configured for emission of microwave energy, wherein the radiating portion is aligned with the radiation window; and
 a cap located at a probe distal end, the cap comprising a cap proximal boundary;
 wherein a length of the radiating portion varies around a circumference of the coaxial cable, the radiating portion further comprising:

a first section having a first length, the first section configured for emission of the microwave energy at a first resonant frequency; and a second section having a second length, the second section configured for emission of the microwave energy at a second resonant frequency that is different from the first resonant frequency.

2. The probe of claim 1 wherein the outer conductor distal boundary varies in distance from the probe distal end around the circumference of the coaxial cable.

3. The probe of claim 1 wherein the cap comprises a metallic material and the cap proximal boundary varies in distance from the probe distal end around the circumference of the coaxial cable.

4. The probe of claim 1 wherein the outer conductor distal boundary and the cap proximal boundary varies in distance from the probe distal end around the circumference of the coaxial cable.

5. The probe of claim 1 wherein the outer conductor distal boundary or the cap proximal boundary comprises a plurality of discrete sections, wherein adjacent discrete sections are at different distances from the probe distal end around the circumference of the coaxial cable.

6. The probe of claim 1 wherein the outer conductor distal boundary or the cap proximal boundary comprises a wave shape around the circumference of the coaxial cable.

7. The probe of claim 1 wherein the outer conductor distal boundary or the cap proximal boundary comprises a saw tooth shape around the circumference of the coaxial cable.

8. The probe of claim 1 wherein the outer conductor distal boundary is a uniform distance from the probe distal end around the circumference of the coaxial cable.

9. The probe of claim 1 wherein the cap proximal boundary is uniform in distance from the distal end of the probe around the circumference of the coaxial cable.

10. The probe of claim 1 further comprising a choke.

11. The probe of claim 1 wherein the shielded portion of the probe body comprises a metal cannula.

12. The probe of claim 11 further comprising a dielectric layer in between the metal cannula and the outer conductor.

13. The probe of claim 11 further comprising a choke comprising:
a choke contact between the metal cannula and the outer conductor; and
a choke length extending between the choke contact and a distal end of the metal cannula.

14. The probe of claim 13 wherein the choke contact or the distal end of the cannula varies in its distance from the probe distal end.

15. The probe of claim 1 wherein the radiation window comprises a portion of the dielectric material of the cable surrounding the radiating portion of the center conductor.

16. The probe of claim 1 wherein the cap further comprises a cap tip configured to pierce tissue at a cap distal end.

17. A microwave ablation system comprising a microwave energy source and a microwave ablation probe, the probe comprising:
a probe body comprising a shielded portion and a radiation window that is at least partially transparent to microwave energy, wherein the probe body further comprises a metal cannula;
a coaxial cable within the probe body connected to the microwave energy source, the cable comprising:
a center conductor,
a dielectric material surrounding the center conductor of the cable, and
an outer conductor having an outer conductor distal boundary,
wherein the center conductor comprises a radiating portion that extends beyond a distal boundary of the outer conductor, wherein the radiating portion is configured for emission of microwave energy, wherein the radiating portion is aligned with the radiation window;
a cap located at a probe distal end, the cap comprising:
a cap tip configured to pierce tissue at a cap distal end, and
a cap proximal boundary; and
a choke comprising:
a choke contact between the metal cannula and the outer conductor; and
a choke length extending between the choke contact and a distal end of the metal cannula; and
wherein a length of the radiating portion varies around a circumference of the coaxial cable, the radiating portion further comprising:
a first section having a first length, the first section configured for emission of the microwave energy at a first resonant frequency; and
a second section having a second length, the second section configured for emission of the microwave energy at a second resonant frequency that is different from the first resonant frequency.

18. The probe of claim 17 wherein the outer conductor distal boundary varies in distance from the probe distal end around the circumference of the coaxial cable.

19. A method of microwave ablation comprising:
providing a microwave ablation probe comprising:
a probe body comprising a shielded portion and a radiation window that is at least partially transparent to microwave energy;
a coaxial cable within the probe body comprising:
a center conductor,
a dielectric material surrounding the center conductor of the cable, and
an outer conductor having an outer conductor distal boundary,
wherein the center conductor comprises a radiating portion that extends beyond a distal boundary of the outer conductor, wherein the radiating portion is configured for emission of microwave energy, wherein the radiating portion is aligned with the radiation window; and
a cap located at a probe distal end, the cap comprising a cap tip configured to pierce tissue at a cap distal end and a cap proximal boundary;
wherein a length of the radiating portion varies around a circumference of the coaxial cable, the radiating portion further comprising:
a first section having a first length, the first section configured for emission of the microwave energy at a first resonant frequency; and
a second section having a second length, the second section configured for emission of the microwave energy at a second resonant frequency that is different from the first resonant frequency; and
delivering microwave energy to the radiating portion.

20. The method of claim 19 wherein the microwave ablation probe produces microwave energy at three or more resonant frequencies.

* * * * *